United States Patent [19]

Cleveland et al.

[11] Patent Number: 5,459,535
[45] Date of Patent: Oct. 17, 1995

[54] COMPACT TELESCOPING RETINOSCOPE

[75] Inventors: William E. Cleveland, Cortland; Ervin Goldfain, Syracuse, both of N.Y.

[73] Assignee: Welch Allyn, Inc., Skaneateles Falls, N.Y.

[21] Appl. No.: 330,631

[22] Filed: Oct. 28, 1994

[51] Int. Cl.$^6$ ..................................................... A61B 3/10
[52] U.S. Cl. ............................ 351/218; 351/216; 351/221
[58] Field of Search ..................................... 351/218, 213, 351/215, 211, 221, 205, 217, 216

[56] References Cited

U.S. PATENT DOCUMENTS

| | | | |
|---|---|---|---|
| 5,189,449 | 2/1993 | Perkins | 351/211 |
| 5,200,772 | 4/1993 | Perkins et al. | 351/213 |
| 5,202,710 | 4/1993 | Perkins | 351/211 |

Primary Examiner—William L. Sikes
Assistant Examiner—Jung Xuan Dang
Attorney, Agent, or Firm—Harris Beach & Wilcox

[57] ABSTRACT

The present invention is directed to a compact retinoscope which telescopes to a closed position in order to allow the instrument to be stored in a pocket or pocket carrying case. As the instrument body or head is pushed downward to its closed position, a main internal sleeve travels upwards (relative to the head) to contact and swing a beam splitter mount positioned within the head of the instrument up into a stored position. In the stored position the reflecting means (beam splitter) of the device are positioned in a secured manner which provides added security against damage to the reflecting means if the instrument or carrying case is accidentally dropped. When the instrument head is pulled to its open or functional position, a wire-form spring positioned within the head biases the beam splitter mount back to its functional position.

7 Claims, 4 Drawing Sheets

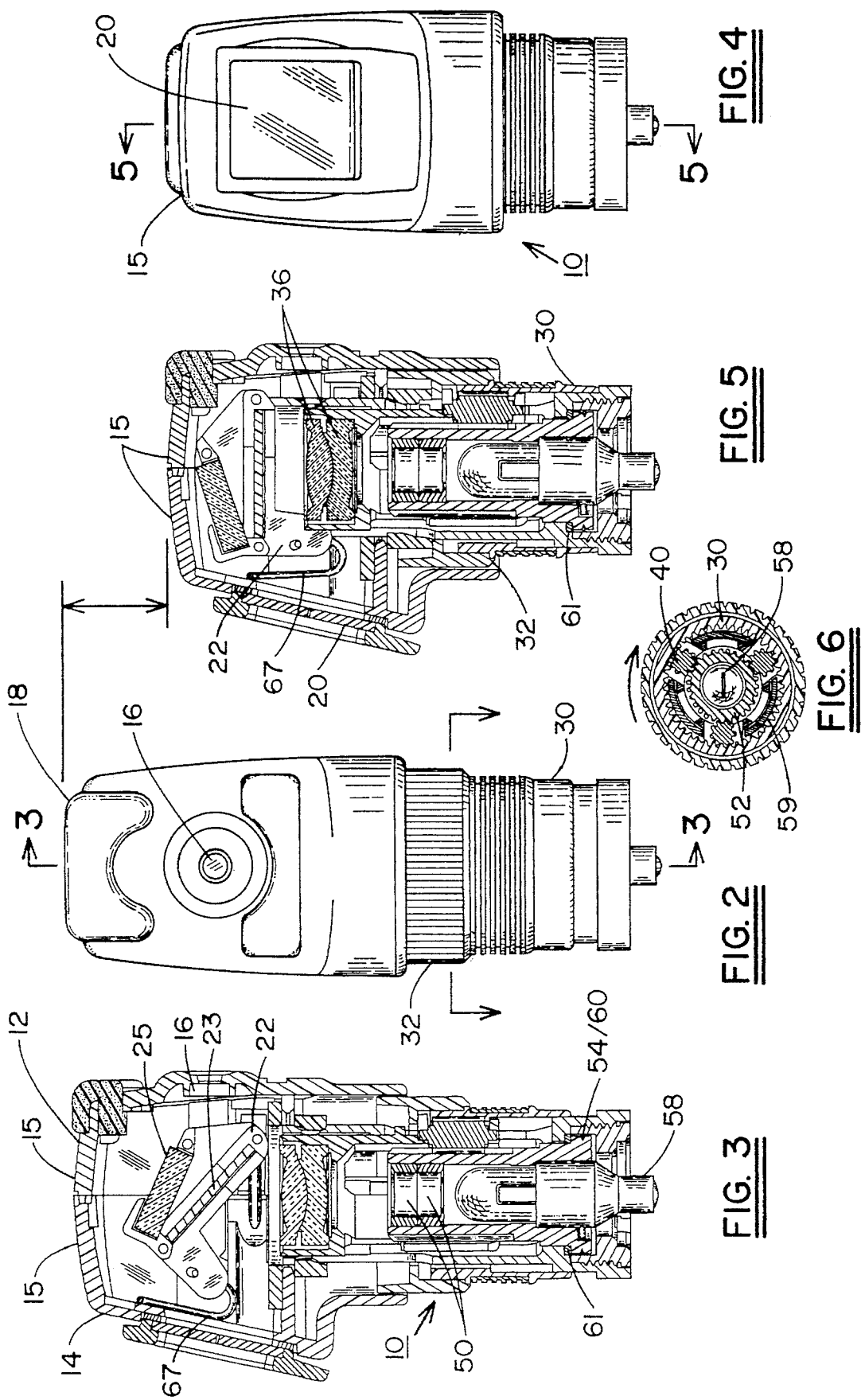

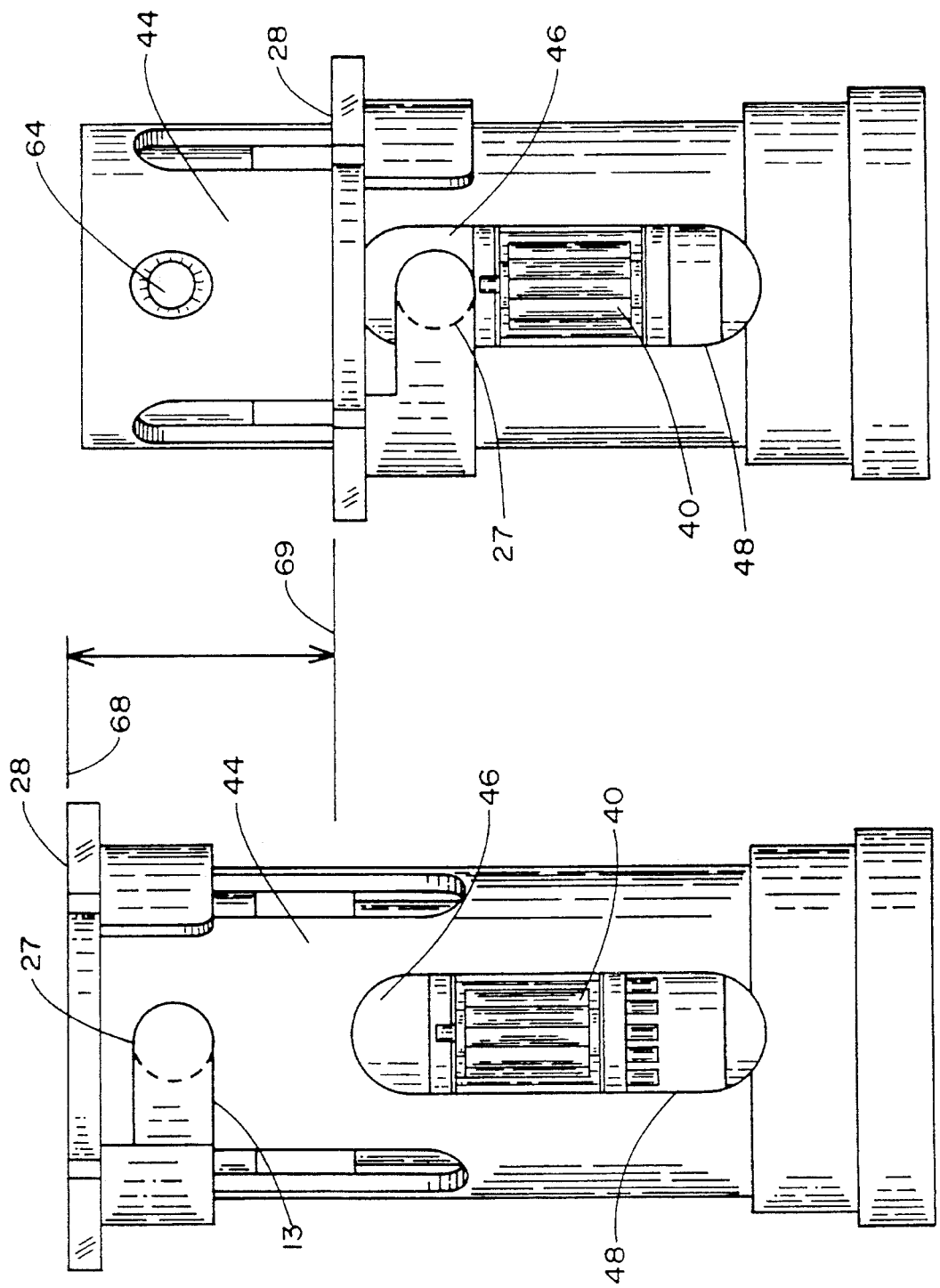

COMPACT TELESCOPING RETINOSCOPE

BACKGROUND OF THE INVENTION

The invention relates to medical diagnostic instruments and more particularly to a telescoping compact retinoscope which can easily be stored in a jacket or coat pocket, or pocket carrying case.

Conventional prior art retinoscopes normally have a nominal length of about 10 inches including the head and handle portion. This typical size makes the instrument inconvenient and unsuitable for storage and carrying in a coat or jacket pocket. It therefore requires that the instrument be stored and secured in a larger carrying case for transport when the doctor is using the retinoscope outside of his office such as conducting visits to clinics, nursing homes, and the like.

There is, therefore, a need in the field for a compact retinoscope which is significantly smaller in size than retinoscopes of the prior art, and which can be easily contained or stored in a pocket or pocket carrying case with a portable power source. In the medical field portable power sources are currently used to power and store other medical and diagnostic instruments such as ophthalmoscopes and retinoscopes. Portable powers of this type are currently being sold by Welch Allyn, Inc. of Skaneateles Falls, N.Y., under the trademark CompacSet™ and Pocketscopes™.

Accordingly, it is an object of the present invention to provide a compact retinoscope having telescoping features which may be conveniently accommodated or stored in a pocket or pocket carrying case, and which overcomes the disadvantages noted above. U.S. Pat. Nos. 5,189,449; 5,200,772; and 5,202,710 are representative of conventional retinoscopes of the prior art, having a size of approximately 4.5 inches in total length.

The minimum length required for the retinoscope of the present invention is at odds with need for the required optical length to provide the optical performance of full size retinoscopes, and therefore presented the need for a telescoping mechanism to accomplish the objectives of the invention.

SUMMARY OF THE INVENTION

The present invention is directed to a compact retinoscope which telescopes to a closed position in order to allow the instrument to be stored in a pocket or pocket carrying case. As the instrument head is pushed downward to its closed position, a main internal sleeve travels upwards and swings a beam splitter mount positioned within the head of the instrument up into a stored position. In the stored position the beam splitter is positioned in a secured manner which provides added protection against damage if the instrument or carrying case is accidentally dropped. When the instrument head is pulled up a wire-formed spring positioned within the head biases the beam splitter mount back to its functional position. An index ring guides and detents the instrument head as it slides up and down on the main sleeve. Stability of the instrument is maintained via guiding the sliding assembly in a pair of outer housings. The design includes a built-in beam splitter and light trap, mounted in one pivotable mount. Dynamic retinoscopy is performed in the conventional manner by hooking MEM cards onto a frame holding the side window of the instrument.

Accordingly, it is an object of the present invention to provide a compact retinoscope having telescoping features which may be conveniently overcoming stored in a pocket or pocket carrying case in which overcomes the disadvantages noted above. U.S. Pat. Nos. 5,189,449; 5,200,772; and 5,202,710 are represented of conventional retinoscopes to the art and having a size of approximately 4.5 inches in total length.

BRIEF DESCRIPTION OF THE DRAWINGS

FIG. 2 is a rear view of one embodiment of the device of the present invention.

FIG. 3 is a cross sectional view taken at 3—3 of FIG. 2.

FIG. 4 is a front view of the device of FIG. 2.

FIG. 5 cross sectional view taken at 5—5 of FIG. 4.

FIG. 6 is a cross sectional view taken at 6—6 of FIG. 2.

FIG. 7 is a side view of the telescoping mechanism of the present invention in the open position.

FIG. 8 is a side view of the device of FIG. 7 in the stored or closed position.

DETAILED DESCRIPTION OF THE DRAWINGS

Figure 9:
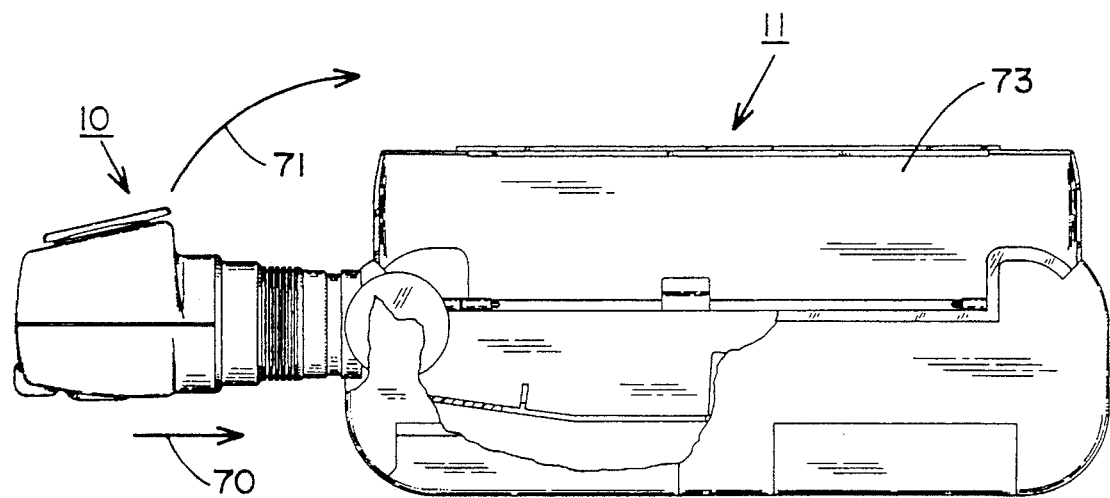
FIG. 9–11 are perspective views of a retinoscope according to one embodiment of the present invention when used with a power source and carrying case.

With reference to the drawings, and initially to FIG. 9, a streak retinoscope 10 according to the present invention is coupled to a portable power source and carrying case 11. Retinoscope 10 contains a main sleeve subassembly, including an external control top sleeve 32 and a bottom control sleeve 30. Top control sleeve 32 and bottom control sleeve 30 form a sleeve subassembly by being joined together by a pressed fit. Lateral gear 59 is molded into sleeve 30 allowing engagement with the three planet gears 40. The instrument head 15 has a viewing port 16 and brow rest 18 on the doctor's side of the instrument (FIG. 2). The head 15 contains two outer covers 12 and 14 mounted side to side and incorporates beam splitter 24 disposed at a 45 degree angle for reflecting the streak of light from the lamp through the window 20 into the patient's eye, and allowing returned images to be viewed directly through beam splitter 24 and the viewing port 16.

A lamp carrier assembly comprises a lamp 58 and a two glare stops 50 whose slots are aligned with the filament in the lamp 58, located in lamp carrier 52. Glare stops 50 mate to each other (via pin hole connection not shown) and are designed to efficiently block internal stray light. An electric contact 54 maintains connection with the lamp 58 for the continuous rotation of the lamp. The contact spring 54 fits in a radial groove in lamp carrier 52 and provides electrical connection between the lamp 58 and threaded insert 56 which in turn interfaces a battery (not shown) through threaded engagement 62 of carrying case 11. The lens holder assembly includes a lens holder 34 surrounding the lamp carrier 52. A main sleeve 44 interfaces the head 15 with an index ring 28, which contains three flexible detenting fingers 13 which contact three recessed dimples 64 in the outer surface of sleeve 42. The top flange 61 section of index ring 28 is contained in fixed engagement with surfaces 65 which are engaged into grooves 66 within a recess formed in both halves 12 and 14 of head 15. The main sleeve 44 further contains three upper vertical slots 41 which index and guide the vertical movement of the main sleeve from a closed to an open position upon sliding of the head 15. The main sleeve 44 also has three lower vertical slots 46 which engage lens holder legs which hold planet gears 40 in place. This arrangement permits the axial movement of the lens holder 34 (which contains lenses 36) relative to the main sleeve 44, but prohibits rotation of the lens holder 34.

As shown in FIGS. 1, 3, 5 and 6, three planet gears 40 are disposed at 120 degree intervals and are carried on the legs 38 of the lens holder 34. The lamp carrier 52 has a wide gear 63 formed on its outer surface, which engages with the teeth of the planet gears 40. On an inner surface of the bottom control sleeve 30, there are formed internal gear teeth 59 which also engage the planet gears 40.

The sleeve grip 31 is placed around the control sleeve lower portion 30.

The legs 38 of the lens holder 34, in addition to carrying the planet gears 40 also extend radially outward sufficient to fit within the annular gap formed by the matting of the two control sleeves 30 and 32. This axially constrains the lens holder 34 so that the latter will move in accordance with corresponding axial motion of the external control sleeve 30 and 32. On the other hand, the planet gears 40 slide freely in the axial direction along the sun gear teeth 63 formed in the lamp carrier 52. This permits the lens holder assembly to be moved axially from a divergent ray position, to a convergent ray position. The lens holder assembly can be moved as appropriate to focus the projected streak or bar without change in the rotation disposition thereof.

Referring to FIG. 6, the planetary gear system including the bottom control sleeve 30, with the internal gear teeth 59 the planet gear 40, and the lamp carrier 52 with its sun gear teeth, rotates the lamp carrier assembly corresponding to rotation of the control sleeve 32. As indicated in FIG. 6 the direction of rotation of the lamp carrier 52 and slotted aperture is reversed from that of the control sleeve 30. That is, clockwise rotation of the control sleeve 30 results in counterclockwise rotation of the lamp carrier 52 assembly, and vice versa.

With this control handle arrangement, the lamp carrier 52 is carried at the proximal end of the control sleeve, preferably in direct contact with the compact power case 11 which contains a battery (not shown). Consequently, the lamp 58 is accessible and can be removed and replaced without difficulty. The lamp 58 rotates approximately twice for each rotation of the control sleeve. Thus, less sleeve motion is needed to rotate the streak.

With the exception of the telescoping mechanism and associated components, the basic operation and structure of the device of the present invention is equivalent to that of the retinoscope disclosed in Assignee's U.S. Pat. No. 5,189,449 which is incorporated herein by reference.

Figure 1:
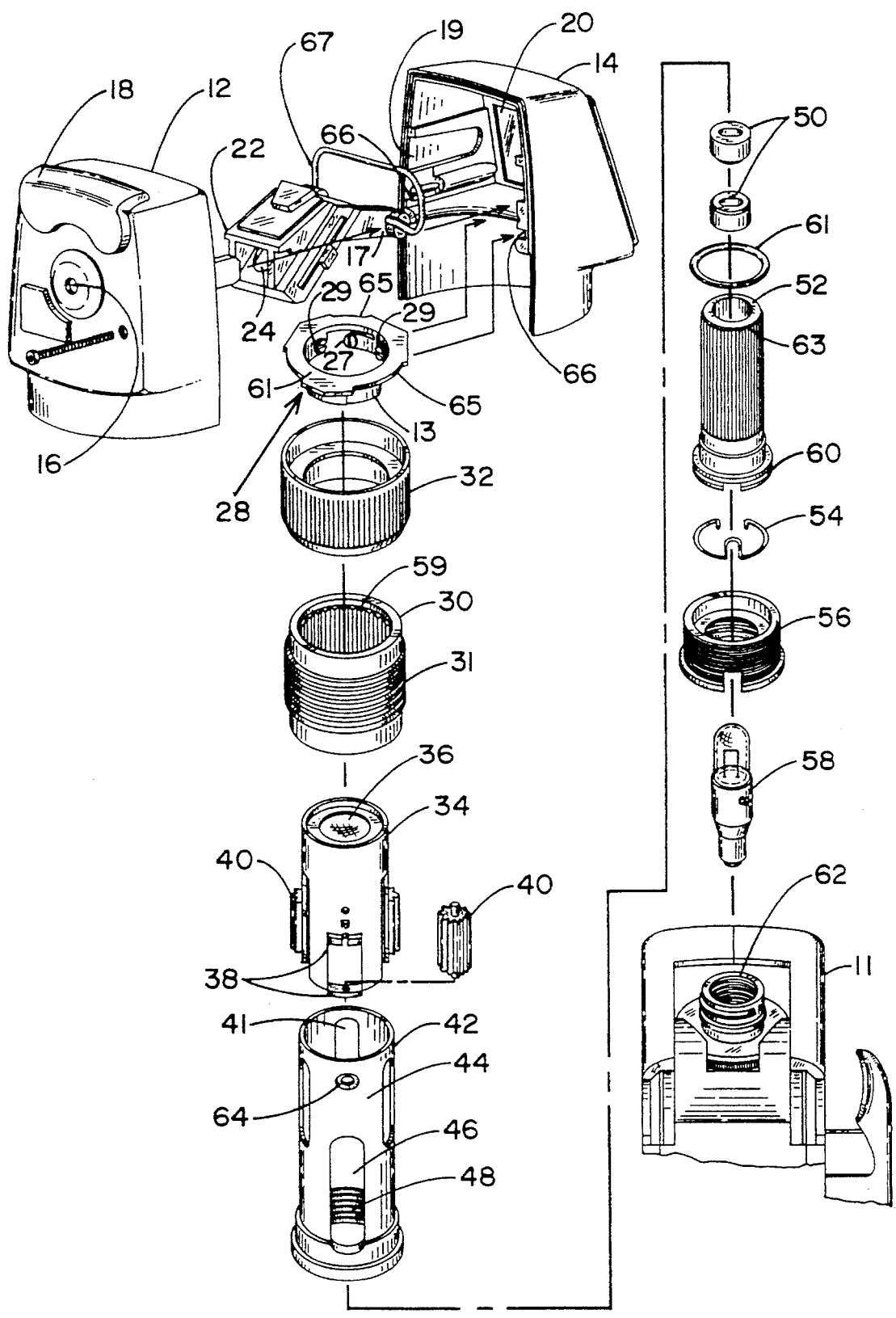
FIG. 1 is an exploded view of a retinoscope according to one embodiment of the invention.

FIG. 1 represents an exploded view which includes all of the basic elements of the retinoscope head of the present invention including the novel telescoping feature which allows the device to be reduced in size to provide the advantages described herein.

In FIGS. 7 and 8, the components of the present invention which allow for the novel telescoping feature of the present invention are set forth. In FIG. 7, components are illustrated in the operative or open position in which index ring 28 containing three detent fingers 13 adapted to be placed and fixed engagement in three recesses or holes, respectively 64 of main sleeve 44. The detent finger each further contain a projection 29 on its inner surface which ride in slot 41 to guide the vertical movement of index ring 28 and a projection 27 which engages recess 64. The index ring 28 is designed to travel from the open position 68 as illustrated in FIG. 7 over main sleeve 44 down to the stored position 69 illustrated in FIG. 8 wherein the index ring designed to travel within three vertical slots 41 contained in main sleeve 44 when downward pressure on the head 15 overcomes the detent fingers contact or friction hold within recesses 64 contained in sleeve 44. As the instrument head 15 is pushed downward to its closed position, main sleeve 44 travels upwards and swings a beam splitter mount 22 positioned within the head of the instrument up into a stored position. In the stored position the (beam splitter 23) and light trap 25 are positioned in a secured manner which provides added protection against damage. The beam splitter mount 22 pivots on a pair of protrusion 17 which travel in recess 19 formed in outer cover 14 of head 15. When the instrument head 15 is pulled up, a wire-formed spring 67 positioned within the head biases the beam splitter mount back to its functional position. The index ring 28 guides and detents the instrument head as it slides up and down on the main sleeve 44. The position of the index ring 28 and main sleeve 44 as illustrated in FIGS. 7 and 8, respectively, corresponds with the overall position of the head and movement of the optics as illustrated, respectively, in FIGS. 3 and 5 of the drawings.

While the retinoscope 10 is shown with a portable power source 11, the present invention clearly also applies to retinoscopes having battery type power handles, cord type handles or those deriving their electrical power by other means.

Figure 10:
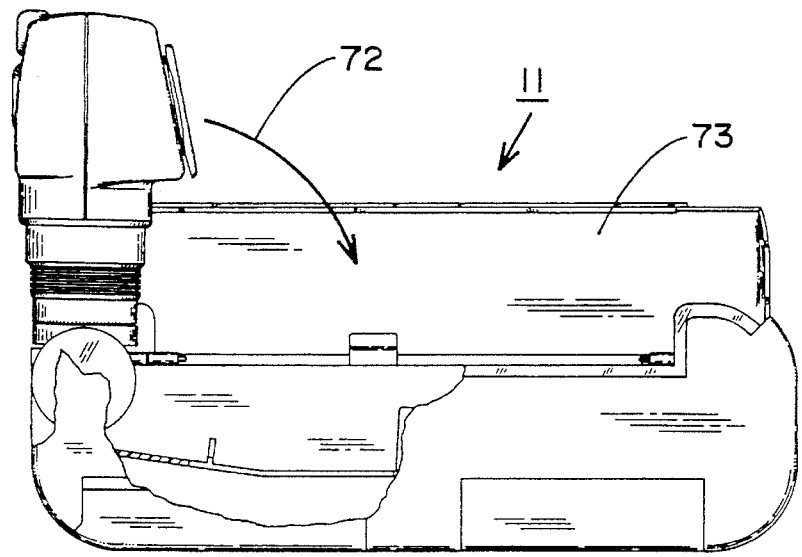
Figure 11:
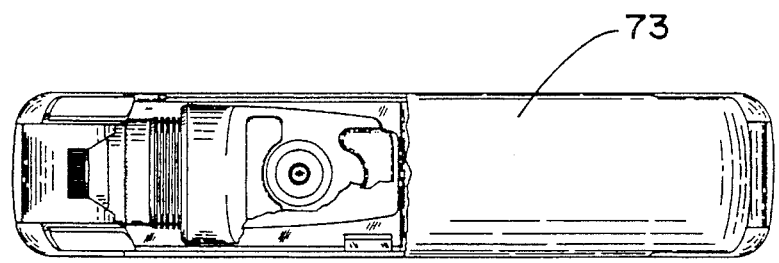

FIG. 9 depicts the storage of retinoscope 10 in the power source carry case 11. To telescope the retinoscope to the closed position the retinoscope 10 is pushed in the direction of arrow 70 until stopped and then swung in the direction of arrow 71. FIG. 10 depicts the movement of streak retinoscope 10 in continued direction of arrow 72. FIG. 11 depicts the completed storage of retinoscope 10 within the power source/carry case 11 with dust cover 73 closed. The retinoscope 10 is connected to case 11 by the internal threads of insert 56 which engage threaded coupling 62. Insert 56 is connected to main sleeve 44 through internal threads 48.

While the invention has been described in detail with reference to a single preferred embodiment, it should be apparent that many modifications and variations would present themselves to those skilled in the art without departing from the scope and spirit of this invention, as defined in the appended claims.

What is claimed is:

1. A compact retinoscope which telescopes from a functional position to a shortened storage position of the type having a body portion containing most of the elements of the optical system, said retinoscope being surrounded by an outer housing with a viewing path passing therethrough, a source of illumination for directing a beam of light along a light path and reflecting means positioned within said body portion for redirecting the light path along the viewing path, the improvement comprising:

a. internal sleeve means positioned centrally within a lower part of said body portion which travels in an upward vertical direction in response to the downward movement of said body portion, and in a downward vertical direction in response to the upward movement of said body portion;

b. reflecting means positioned within said body portion moveable from a functional position to a stored position in response to the upward movement of said internal sleeve means; and c. means adjacent said reflecting means to automatically move said reflecting means from said stored position to said functional position in response to said sleeve being moved to its downward position.

2. The retinoscope of claim 1 in which the travel and indexing of the internal sleeve means and body portion is controlled by a cylindrical bracket which surrounds said internal sleeve.

3. The retinoscope of claim 2 in which said bracket contains a plurality of detenting fingers which guide and index the instrument head as it slides up and down on said internal sleeve.

4. The retinoscope of claim 1 in which the reflecting means is pivotably mounted for movement from the functional to the stored position.

5. The retinoscope of claim 4 in which spring means return the reflecting means from the stored to the functional position in response to the downward movement of said internal sleeve.

6. A compact retinoscope which telescopes from a functional position to a shortened storage position of the type having a body portion containing most of the elements of the optical system, and a lower neck portion integrally connected thereto which is adapted to be releasably connected to a battery handle or equivalent source of power; said retinoscope being surrounded by an outer housing with a viewing path passing therethrough, a source of illumination for directing a beam of light along a light path and reflecting means positioned within said body portion for redirecting the light path along the viewing path, the improvement comprising:

a. internal sleeve means positioned centrally within a lower part of said body portion which travels in an upward vertical direction in response to the downward movement of said body portion and in a downward vertical direction in response to the upward movement of said body portion with the travel and indexing of the internal sleeve means and body portion being controlled by a bracket which surrounds said internal sleeve and which is held in fixed engagement within said body portion;

b. reflecting means pivotably mounted within said body portion moveable from a functional position to a stored position in response to the upward movement of said internal sleeve means; and c. spring means adjacent said reflecting means to automatically move said reflecting means from said stored position to said functional position in response to said sleeve being moved to its downward position.

7. The retinoscope of claim 6 in which said bracket contains a plurality of detenting fingers which guide and index the instrument body as it slides up and down on said internal sleeve.

* * * * *